United States Patent
Girard et al.

(10) Patent No.: US 8,277,425 B2
(45) Date of Patent: Oct. 2, 2012

(54) DUAL LUMEN PORT WITH F-SHAPED CONNECTOR

(75) Inventors: Mark Girard, Waltham, MA (US); Benjamin Bell, Haverhill, MA (US); Todd Beaupre, Reading, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 2134 days.

(21) Appl. No.: 10/807,590

(22) Filed: Mar. 24, 2004

(65) Prior Publication Data

US 2005/0215960 A1  Sep. 29, 2005

(51) Int. Cl.
  *A61M 31/00* (2006.01)
  *A61M 37/00* (2006.01)
(52) U.S. Cl. .................................. 604/288.04
(58) Field of Classification Search ............ 604/288.01–288.04, 284, 533–539, 890.1, 891.1
  See application file for complete search history.

(56) References Cited

U.S. PATENT DOCUMENTS

| | | |
|---|---|---|
| 3,159,175 A | 12/1964 | Macmillan |
| 3,477,438 A | 11/1969 | Allen et al. |
| 3,525,357 A | 8/1970 | Koreski |
| 3,541,438 A | 11/1970 | Nelsen et al. |
| 3,669,323 A | 6/1972 | Harker et al. |
| 3,674,183 A | 7/1972 | Venable et al. |
| 3,811,466 A | 5/1974 | Ohringer |
| 3,853,127 A | 12/1974 | Spademan |
| 3,955,594 A | 5/1976 | Snow |
| 3,971,376 A | 7/1976 | Wichterle |
| 4,143,853 A | 3/1979 | Abramson |
| 4,447,237 A | 5/1984 | Frisch et al. |
| 4,543,088 A | 9/1985 | Bootman et al. |
| 4,610,665 A | 9/1986 | Matsumoto et al. |
| 4,692,146 A | 9/1987 | Hilger |
| 4,772,270 A | 9/1988 | Waiita et al. |
| 4,781,680 A | 11/1988 | Redmond et al. |
| 4,802,885 A | 2/1989 | Weeks et al. |
| 4,857,053 A | 8/1989 | Dalton |
| 4,886,501 A | 12/1989 | Johnston et al. |
| 4,886,502 A | 12/1989 | Poirier et al. |
| 4,892,518 A * | 1/1990 | Cupp et al. ............... 604/288.02 |
| 4,897,081 A | 1/1990 | Poirier et al. |
| 4,904,241 A | 2/1990 | Bark |
| 4,908,029 A | 3/1990 | Bark et al. |

(Continued)

FOREIGN PATENT DOCUMENTS

CA  2399057  8/2001

(Continued)

*Primary Examiner* — Matthew F DeSanto
(74) *Attorney, Agent, or Firm* — Bingham McCutchen LLP

(57) ABSTRACT

A port for subcutaneous implantation, comprising a housing including first and second wells formed therein and a substantially F-shaped flow element including first and second lumens extending therethrough wherein, when in an operative configuration the F-shaped flow element is coupled to the housing with a proximal end of each of the lumens in fluid communication with a respective one of the first and second wells for receiving fluid therefrom, and wherein distal ends of each of the lumens form outlets, each outlet being coupleable to a lumen of a medical catheter, the F-shaped flow element including first and second arms extending from a trunk with the first lumen extending through the first arm to the trunk and the second lumen extending through the second arm to the trunk, the first and second lumens being separated from one another within the trunk.

7 Claims, 2 Drawing Sheets

U.S. PATENT DOCUMENTS

| | | |
|---|---|---|
| 4,929,236 A | 5/1990 | Sampson |
| 5,009,391 A | 4/1991 | Steigerwald |
| 5,009,644 A | 4/1991 | McDonald |
| 5,045,060 A | 9/1991 | Melsky et al. |
| 5,053,013 A | 10/1991 | Ensimger et al. |
| 5,059,186 A | 10/1991 | Yamamoto et al. |
| 5,069,206 A | 12/1991 | Crosbie |
| 5,084,015 A | 1/1992 | Moriuchi |
| 5,092,849 A | 3/1992 | Sampson |
| 5,129,891 A | 7/1992 | Young |
| 5,137,529 A | 8/1992 | Watson et al. |
| 5,147,483 A | 9/1992 | Melsky et al. |
| 5,167,638 A | 12/1992 | Felix et al. |
| 5,180,365 A | 1/1993 | Ensminger et al. |
| 5,205,834 A | 4/1993 | Moorehead et al. |
| 5,242,415 A | 9/1993 | Kantrowitz et al. |
| 5,249,598 A | 10/1993 | Schmidt |
| 5,263,930 A | 11/1993 | Ensminger |
| 5,281,199 A | 1/1994 | Ensminger et al. |
| 5,312,337 A | 5/1994 | Flaherty et al. |
| 5,318,545 A | 6/1994 | Tucker |
| 5,350,360 A | 9/1994 | Ensminger et al. |
| 5,352,204 A | 10/1994 | Ensminger |
| 5,356,381 A | 10/1994 | Ensminger et al. |
| 5,387,192 A | 2/1995 | Glantz et al. |
| 5,396,925 A | 3/1995 | Poli et al. |
| 5,399,168 A | 3/1995 | Wadsworth et al. |
| 5,417,656 A | 5/1995 | Ensminger et al. |
| 5,423,334 A | 6/1995 | Jordan |
| 5,453,097 A | 9/1995 | Paradis |
| 5,476,451 A | 12/1995 | Ensminger et al. |
| 5,520,643 A | 5/1996 | Ensminger et al. |
| 5,527,277 A | 6/1996 | Ensminger et al. |
| 5,527,278 A | 6/1996 | Ensminger et al. |
| 5,531,684 A | 7/1996 | Ensminger et al. |
| 5,542,923 A * | 8/1996 | Ensminger et al. ...... 604/288.03 |
| 5,554,117 A | 9/1996 | Ensminger et al. |
| 5,556,381 A | 9/1996 | Ensminger et al. |
| 5,558,641 A | 9/1996 | Galntz et al. |
| 5,562,618 A | 10/1996 | Cai et al. |
| 5,607,393 A | 3/1997 | Ensminger et al. |
| 5,613,945 A | 3/1997 | Cai et al. |
| 5,662,616 A | 9/1997 | Bousquet |
| 5,707,357 A | 1/1998 | Mikhail et al. |
| 5,741,228 A | 4/1998 | Lambrecht et al. |
| 5,755,780 A | 5/1998 | Finch et al. |
| 5,792,104 A | 8/1998 | Speckman et al. |
| 5,792,123 A | 8/1998 | Ensminger |
| 5,797,886 A | 8/1998 | Roth et al. |
| 5,814,016 A | 9/1998 | Valley et al. |
| 5,848,989 A | 12/1998 | Villani |
| 5,879,322 A | 3/1999 | Lattin et al. |
| 5,882,341 A | 3/1999 | Bousquet |
| 5,897,528 A | 4/1999 | Schultz |
| 5,906,596 A | 5/1999 | Tallarida |
| 5,911,706 A | 6/1999 | Estabrook et al. |
| 5,941,856 A | 8/1999 | Kovacs et al. |
| 5,944,688 A | 8/1999 | Lois |
| 5,944,698 A | 8/1999 | Fischer et al. |
| 5,954,687 A | 9/1999 | Baudino |
| 5,954,691 A | 9/1999 | Prosl |
| 5,961,497 A | 10/1999 | Larkin |
| 5,989,216 A | 11/1999 | Johnson et al. |
| 6,056,717 A | 5/2000 | Finch et al. |
| 6,086,555 A | 7/2000 | Eliasen et al. |
| 6,099,508 A | 8/2000 | Bousquet |
| 6,152,909 A | 11/2000 | Bagaoisan et al. |
| 6,190,352 B1 | 2/2001 | Haarala et al. |
| 6,210,366 B1 | 4/2001 | Sanfilippo |
| 6,287,293 B1 | 9/2001 | Jones et al. |
| 6,306,124 B1 | 10/2001 | Jones et al. |
| 6,527,754 B1 | 3/2003 | Tallarida et al. |
| 6,592,571 B1 | 7/2003 | Verbeek et al. |
| 6,610,031 B1 | 8/2003 | Chin |
| 6,726,063 B2 | 4/2004 | Stull et al. |
| 6,962,577 B2 * | 11/2005 | Tallarida et al. ......... 604/288.02 |

FOREIGN PATENT DOCUMENTS

| | | |
|---|---|---|
| EP | 0128525 | 12/1984 |
| EP | 0 343 910 | 11/1989 |
| EP | 0366814 | 5/1990 |
| EP | 0858814 | 8/1998 |
| FR | 2508008 | 12/1982 |
| FR | 2809315 | 11/2001 |
| GB | 0966137 | 8/1964 |
| GB | 2102398 | 2/1983 |
| WO | WO-92/06732 | 4/1992 |
| WO | WO-94/05351 | 3/1994 |
| WO | WO-95/16480 | 6/1995 |
| WO | WO-97/01370 | 1/1997 |
| WO | WO-97/23255 | 7/1997 |
| WO | WO-97/26931 | 7/1997 |
| WO | WO-98/18506 | 5/1998 |
| WO | WO-99/42166 | 8/1999 |
| WO | WO-00/12171 | 3/2000 |
| WO | WO-00/16844 | 3/2000 |
| WO | WO-00/44419 | 8/2000 |

\* cited by examiner

DUAL LUMEN PORT WITH F-SHAPED CONNECTOR

BACKGROUND OF THE INVENTION

Medical procedures for the treatment of chronic diseases often require repeated and prolonged access to a patient's vascular system to inject therapeutic compounds and/or to obtain blood samples. Kidney dialysis, chemotherapy and other chronic treatments may have to be performed several times a week. However it is impractical and dangerous to insert and remove a catheter and a needle from the patient's vein at every session. Thus, these catheters are generally implanted semi permanently with a distal end remaining within the patient in contact with the vascular system and a proximal end remaining accessible from outside the patient's body. A port may be used to access the proximal end of the catheter from outside the body, for example, via a syringe. In many cases, such ports are implanted subcutaneously in the arm or chest to provide protection to the port while maintaining easy access thereto. Such ports typically consist of a housing with one or more wells to receive therapeutic agents.

Under certain conditions, it may be necessary to infuse therapeutic agents (e.g., chemotherapy agents) that are not compatible with one another. In some cases, the therapeutic agents are fluids that cannot be mixed together outside of the body, but which preferably are infused together. These unmixable fluids may lose their potency or may become toxic if mixed prior to infusion in the body. They are therefore kept separate until they reach the blood stream. To address this difficulty, a separate catheter may be used for each of the fluids with distal ends of the catheters (i.e., outlets) near one another. Alternatively, a multi-lumen catheter (e.g., a dual lumen catheter) may be used, with each lumen transporting a different fluid.

Providing two unmixable therapeutic fluids to a dual lumen catheter or to two separate catheters near each other presents challenges as a conventional port may not be useable to inject both fluids. Multiple. ports are generally not implanted near one another because of the surgery required to insert each port and additional complications that may arise with respect to each port. For these purposes a dual well port device having two ports formed within a single housing may be used with each port being connected to a different catheter or to a different lumen of a dual lumen catheter. However, conventional dual well port devices are larger than single port devices, and may require more extensive surgery to be placed in the patient's body. The connections between the wells and the catheter further increase the width of the dual well port, so that a larger incision is often necessary to place such a port within the patient.

SUMMARY OF THE INVENTION

The present invention is directed to a port for subcutaneous implantation, comprising a housing including first and second wells formed therein and a substantially F-shaped flow element including first and second lumens extending therethrough wherein, when in an operative configuration the F-shaped flow element is coupled to the housing with a proximal end of each of the lumens in fluid communication with a respective one of the first and second wells for receiving fluid therefrom, and wherein distal ends of each of the lumens form outlets, each outlet being coupleable to a lumen of a medical catheter, the F-shaped flow element including first and second arms extending from a trunk with the first lumen extending through the first arm to the trunk and the second lumen extending through the second arm to the trunk, the first and second lumens being separated from one another within the trunk.

The present invention is further directed to a dual well port device comprising a housing defining first and second wells disposed along an axis of the housing in combination with an F-shaped flow element including first and second lumens independent of one another, the first lumen, when the flow element is in an operative configuration coupled to the housing, being fluidly connected to the first well and having an arm portion extending at a first angle relative to the axis and wherein, when in the operative configuration, the second lumen is fluidly connected to the second well and includes an arm portion extending at a second angle relative to the axis, the F-shaped flow element including a trunk enclosing trunk portions of the first and second lumens.

The present invention is further directed to a method of infusing fluids into a patient, comprising implanting distal ends first and second catheter lumens into a blood vessel and fluidly connecting each of the first and second catheter lumens to first and second flow element lumens of an F-shaped flow element, the first flow element lumen extending through the trunk and through the first arm to fluidly connect to a first well of a dual well port and the second flow element lumen extending through the trunk and the second arm to a second F arm to fluidly connect to a second well of the port, wherein the first and second flow element lumens are separated from one another in the trunk in combination with introducing a first fluid into the first well and introducing a second fluid into the second well so that the first and second fluids are passed to the blood vessel without intermingling with one another prior to leaving the distal ends of the first and second catheter lumens.

DETAILED DESCRIPTION

Figure 1:
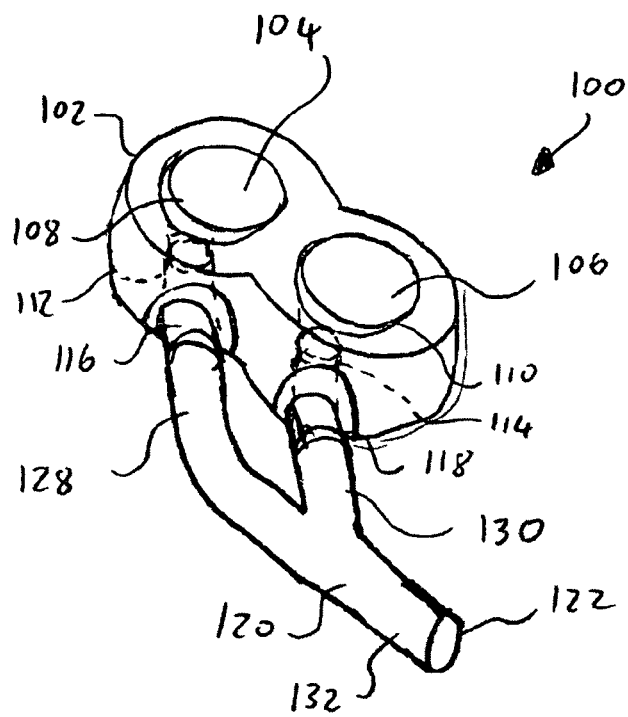
FIG. 1 is a perspective view of a dual well port according to an embodiment of the present invention.

The present invention may be further understood with reference to the following description and the appended drawings, wherein like elements are referred to with the same reference numerals. The present invention is related to medical devices that are used to access the vascular system of a patient. In particular, the present invention relates to access ports used to inject therapeutic agents into the vascular access devices.

As described above, semi-permanent central catheters may be kept in place for extended periods of time—up to two years or more. Central catheters generally comprise a flexible elongated portion that is tunneled or otherwise placed within the patient's body in fluid contact with a blood vessel. The proximal end of such a central catheter may be connected to a port placed subcutaneously in the arm or chest of the patient to selectively provide access to the catheter. These ports often include a self sealing surface (e.g., a septum) that can be pierced by a needle passing through the skin, for injection of therapeutic agents thereinto. Examples of implantable catheters include the catheters manufactured by Vaxcel™, such as the Chronic Dialysis Catheter and the Implantable Vascular Access System.

In a dual well port, separate wells are maintained to separate fluids which are to be presented separately to the bloodstream—i.e., which are not to mix together prior to entering the bloodstream. As described above, certain chemicals may react negatively if mixed together outside of the bloodstream or may lose their potency, etc. Each of the fluids is injected into a corresponding one of the wells through a corresponding septum for the well (or through a portion of a common septum corresponding to the particular well) so that no mixing occurs in the port device. The lumens leading from each of the wells to the catheter (or catheters) also are separate and independent and, due to the size of the wells, are often disposed far apart from one another. The separation of the lumens in conventional dual well port devices has lead to increased bulk and a larger cross sectional area of such port devices. This increased size, consequently, requires proportionally larger incisions through which the port devices are to be subcutaneously implanted, lengthening recovery times, increasing the chances of post-surgical complications and making scarring more extensive. Embodiments of the present invention provide for a configuration of the wells and lumens of a port device that allow a narrower cross section of the device, and therefore allows for a smaller incision through which the port device is implanted.

According to exemplary embodiments of the present invention, a dual well port device is provided which comprises a pair of independent lumens, each extending from a corresponding one of the wells to the periphery of a well housing. The housing lumens are shaped and oriented to reduce a width of the port device itself and are independent so that the fluid in one lumen does not mix with that in the other lumen. A substantially F-shaped flow element, a proximal end of which attaches to the housing, comprises a pair of independent lumens each of which fluidly connects to a corresponding one of the housing lumens. A distal end of the F-shaped flow element connects to the proximal end of a dual lumen catheter (or to the proximal ends of two independent catheters) the distal end of which extends to the patient's vascular system. The configuration of the F-shaped flow element also reduces a frontal area of the dual well port device without sacrificing the flow carrying capacity of the port device. To reduce a width of the port device, the housing lumens are preferably angled relative to an axis of the port along which the two wells are disposed so that the F-shaped flow element may be placed in close proximity to a side surface of the port housing.

In the exemplary embodiment shown in the drawings, the housing's lumens are separate from the lumens defined by the F-shaped flow element. In this example, the F-shaped flow element is a separate component, such as a connector that can be attached to the housing of the port device before or during surgical procedure to implant the port. In a different embodiment, the F-shaped flow element may be an integral part of the port's housing, such that a single lumen may extend from each of the wells to the dual lumen catheter or pair of catheters. The F-shaped flow element thus may be a connector separate and independent from the housing of the port device, or may be an integral part of the housing, depending on the requirements of the situation being addressed and on the construction details of the dual well port device.

The exemplary dual well port according to the present invention comprises two separate wells and two separate septa that form independent flow chambers within the dual well port housing. Likewise, the lumens extending through the housing from each of the wells and through the F-shaped flow element form flow passages that are independent and isolated from one another, so fluids injected into the wells do not mix until the fluids have left the distal end of a catheter coupled to the port device. As described, the disposition of the individual lumens extending from the wells and of the F-shaped flow element are preferably selected to minimize the cross-sectional profile of the port device. For instance, the lumens may extend at a selected angle from the wells as described below, to reduce the profile area of the port device and to maintain the flow carrying capacity of the lumens. Similarly, the length and orientation of the F-shaped flow element may be varied to optimize the size and flow carrying capacity of the port device while providing a simple connection to the catheter(s) leading to the patient.

Figure 2:
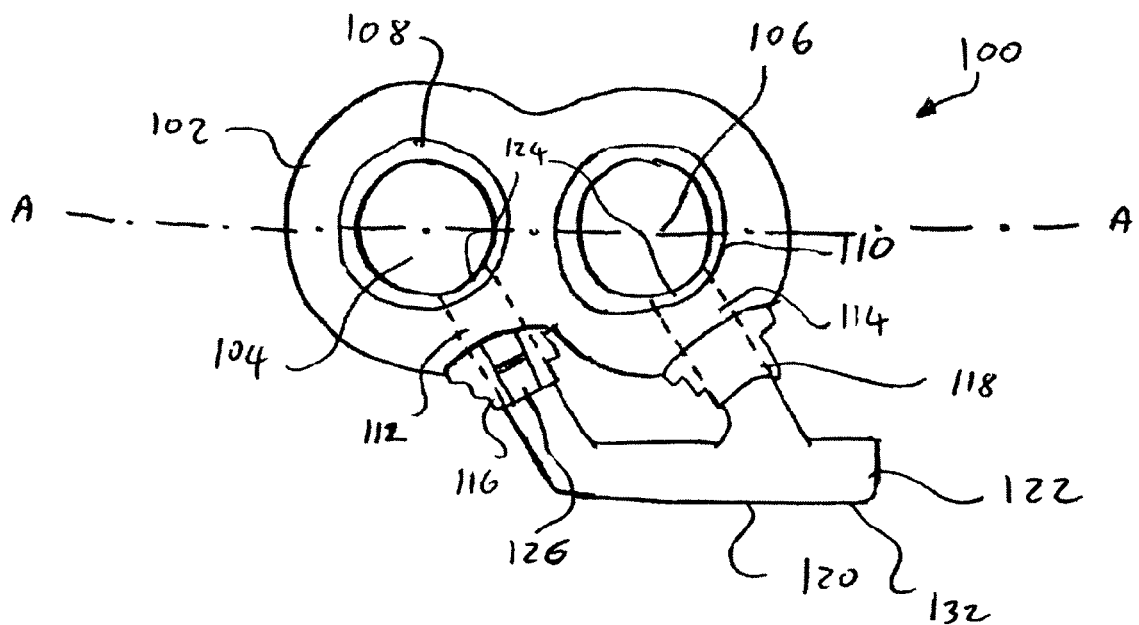
FIG. 2 is a top plan view of the dual well port according the embodiment of the present invention shown in FIG. 1.

As shown in FIGS. 1 and 2, an exemplary dual well port device 100 comprises a housing 102 which defines two wells—a first well 104 and a second well 106. Each of the wells 104, 106 includes an opening on its top side through which a fluid may be introduced into the corresponding well. Septums 108, 110, respectively seal the openings of the wells 104, 106 and prevent fluid therein from leaking out of the port device 100. As would be understood by those skilled in the art, the septums 108, 110 are preferably formed of a flexible, self sealing material which can be punctured repeatedly by a syringe's needle while retaining the ability to self-seal the puncture opening once the needle has been removed. This allows the septums 108, 110 to be punctured repeatedly for injections of fluid thereto while maintaining an effective seal so that the port device 100 may be used for multiple injections of fluid. Each of the septums 108, 110 also forms a seal around the needle used to inject the fluids, so that a positive pressure may be applied through the needle to the fluid, e.g., to drive the fluid from the port device 100 into a catheter attached thereto and into the bloodstream.

As shown in the drawings, a first lumen 112 extends from and is in fluid connection with the first well 104 and a second lumen 114 extends from and is in fluid communication with the second well 106. The first and second lumens 112, 114 are separate and independent of one another and the first and second wells 104, 106 are separate and independent from one another so that there is no fluid communication between the combination of the first lumen 112 with the first well 104 and the combination of the second lumen 114 and the second well 106. The location of the openings 124 of each of the first and second lumens 112, 114 into the corresponding one of the first and second wells 104, 106 and the angle at which these lumens 112, 114 meet their corresponding wells 104, 106 are preferably selected to provide a small profile to the port device 100. For example, the lumens 112, 114 are preferably disposed at an angle of between approximately 30° to approximately 60° from a longitudinal axis A-A of the port device 100. The axis A-A may also be the axis along which the wells 104, 106 are disposed. For a selected angular orientation of the lumens 112, 114, the location of the openings 124 may be optimized so that flow from inside the wells 104, 106 to the corresponding one of the first and second lumens 112, 114 is not impeded. As would be understood by those skilled in the art, the diameter of the lumens 112, 114 is preferably selected to provide a sufficient flow of fluid therethrough based on, for example, the flow requirement of the treatments for which the port device 100 is intended. Although larger diameter lumens handle higher flow rates, those skilled in the art will understand that the desired diameter may be limited by structural considerations related to, for example, the required strength of the housing 102 and by size constraints placed on the device 100.

Fluid injected into the well 104 passes through the corresponding lumen 112 to the catheter via the F-shaped flow element 120. Similarly, fluid injected into the well 106 passes through the lumen 114 to a catheter via the F-shaped flow element 120. The F-shaped flow element 120 includes a pair of arms 128, 130 extending from a trunk 132 and defining a gap 109 between an outer surface of the port device 100, the trunk 132 and the arms 128, 130. Those skilled in the art will understand that the substantial F-shape of the F-shaped flow element 102 does not require that this element precisely mimic the letter F. Rather, the F-shape of the flow element 102 refers more generally to a configuration where 2 arms project from a common trunk substantially parallel to one another at an angle (e.g., of between 15° and 75°) with respect to a longitudinal axis of the trunk. Each of the arms 128, 130 connects to a corresponding one of the lumens 112, 114 so that fluid from each of the lumens 112, 114 passes from the port device 100 into a corresponding one of two flow passages (lumens) formed in the trunk 132 to an outlet 122 while remaining separate from one another. As would be understood by those skilled in the art, the outlet 122 may comprise an adapter designed to connect with an inlet of a catheter, for example, a dual lumen catheter.

The length of the arms 128, 130 may be selected to reduce the profile of the port device 100, for example by selecting a length of the trunk 132 to be a minimum distance which avoids interference with the housing 102. The angle at which the arms 128, 130 project from the trunk 132 is also preferably selected to achieve the same goal. In one example, each of the arms 128, 130 extends along an axis substantially aligned with an axis of the corresponding one of the lumens 112, 114 to reduce flow resistance within the F-shaped flow element 120. However, variations from that orientation may be desirable to construct a more compact port device 100. For example, the arms 128, 130 (and in some cases the lumens 112, 114) may be curved or may have a varying angular orientation to minimize the width of the port device 100. The trunk 132 may be substantially parallel to the longitudinal axis A-A of port 100, or alternatively may be disposed at an angle thereto, as dictated by the requirements of the port device 100.

According to the exemplary embodiment shown in FIGS. 1 and 2, the outlets 116, 118 are disposed at the ends of lumens 112, 114, respectively, at the periphery of the housing 102. In this embodiment, the outlets 116, 118 may be used as adapters to connect the arms 128, 130 respectively to the lumens 112, 114. These connections may be releasable or may be permanent, depending on the specific requirements of the port device 100. The manufacturing of the port device 100 may be simplified by using the F-shaped flow element 120 as a separate connector which attaches to the outlets 116, 118. In this case, the housing 102 and the F-shaped flow element 120 may be formed separately and assembled later in a finishing operation. The ability to form the housing 102 and the F-shaped flow element 120 separately also simplifies tailoring the port device 100 to different applications, since an F-shaped flow element 120 for a particular application (e.g., assembly with a particular housing 102) may be selected from a group including an assortment of lengths and arm orientations to achieve a desired overall size and shape of the port device 100.

In the described embodiment, valves 126 may be included in each of outlets 116, 118. Each valve 126 may be, for example, a pressure actuated safety valve (PASV) which restricts flow through the outlets under certain conditions and allows flow therethrough under preselected flow conditions. For example, when the pressure of the fluid is below a predetermined threshold level, a flow control membrane in the PASV prevents the fluid from flowing therethrough. However, when the fluid pressure is increased above the threshold level, the membrane opens and lets the flow pass. Alternatively, the valves 126 may be of types other than PASV's. For example, a check valve, a spring loaded valve or other type of flow control device may be used, to prevent fluid leakage, to control a direction of fluid flow and/or to control fluid pressure and flow rate. In a different embodiment, one or more flow control devices, such as a valve 126, may be disposed at one or more locations within the F-shaped flow element 120, such as, for example, near the outlet 122.

Figure 3:
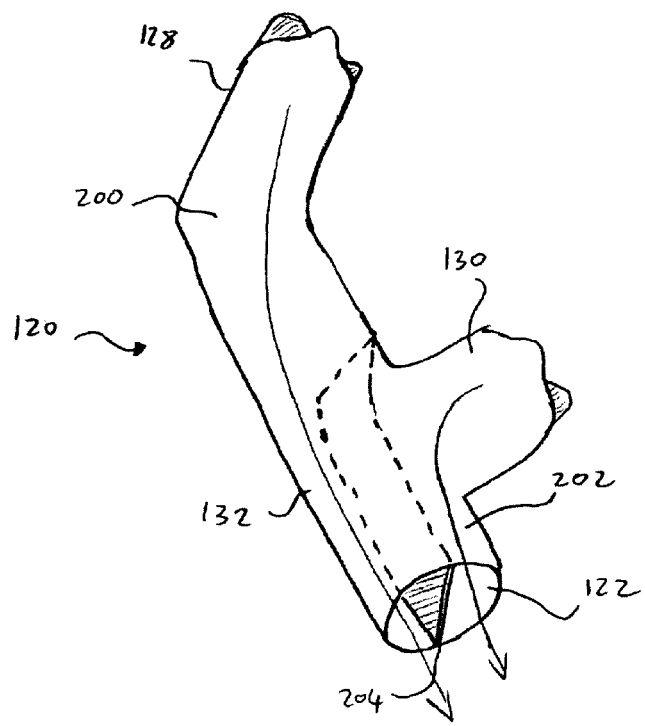
FIG. 3 is a detail view of an F-shaped flow element according to an embodiment of the present invention.

FIG. 3 shows a detail perspective view of an F-shaped flow element 120 according to an embodiment of the invention. As shown, a first arm 128 defines a lumen adapted to fluidly connect with the well 104 of the port device 100 via the corresponding housing lumen 112 such that fluid injected into the well 104 travels to the outlet 122. Similarly, the second arm 130 defines another lumen connected to the second well 106 of the port device 100. As described above, the trunk 132 is divided into two independent lumens so that fluid from each of the wells 104, 106 reaches the outlet 122 without mixing with the fluid from the other well. For example, a partition 204 extends across an interior space of the trunk 132 to separate this space into independent lumens 200 and 202. The lumen 200 couples to the lumen in the arm 128 while the lumen 202 couples to the lumen in the arm 130. As would be understood by those skilled in the art, the partition 204 may be streamlined to minimize blockage and the turbulence imparted to flow through the lumens 200, 202.

In the embodiment shown in FIG. 3, the F-shaped flow element 120 comprises a trunk 132 that has a substantially circular cross section. Here, the partition 204 divides the trunk 132 into two lumens having substantially semi-circular cross sections. In other embodiments, the cross-section of the trunk 132 and of the individual lumens may be modified, to obtain desired cross sectional area and flow characteristics of the port device 100. For example, the lumens 200, 202 may be substantially elliptical, oval or of any other shape suitable to pass a desired flow rate of fluid therethrough. Of course, those skilled in the art will understand that manufacturing an F-shaped flow element with a more complex lumen in the trunk thereof may increase the difficulty and cost of construction relative to the simpler circular trunk described above.

Figure 4:
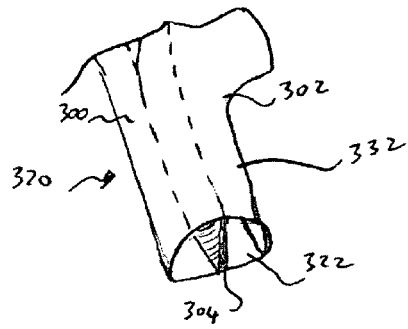
FIG. 4 is a detail view of an F-shaped flow element according to another embodiment of the invention.

FIG. 4 shows an exemplary alternate embodiment of an F-shaped flow element 320, where the trunk 332 has a substantially semi-circular cross section. In this example, a partition 304 defines two independent lumens 300, 302 each of which has a substantially quarter circle cross-sectional shape. This configuration may be advantageous in cases where the overall thickness of the F-shaped flow element 320 is restricted to a predetermined level and/or where special packaging considerations of the port device 100 dictate such a shape or thickness.

Figure 5:
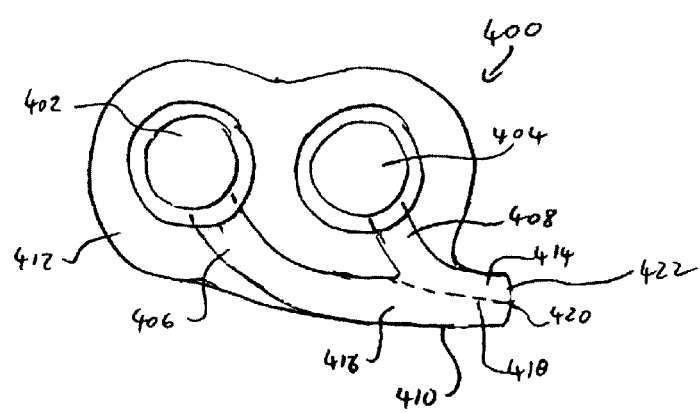
FIG. 5 is a top plan view of a different embodiment of the dual well port device according to the invention.

A different exemplary embodiment of the present invention is shown in FIG. 5. Here, a dual well port device 400 comprises two wells 402, 404 that are fluidly connected to an F-shaped flow element 410 which is integral with a housing 412 of the port device 400. In this exemplary embodiment, arms 406, 408 are also integrally formed with the housing 412 with each extending from a respective one of the wells 402, 404 to the trunk 418. A partition 420 may be used to divide the trunk 418 into independent lumens 414, 416, which maintain the fluids injected into the two wells 402, 404 separate at least until reaching an outlet 422 of the F-shaped flow element 410. As in the embodiments discussed above, the outlet 422 may be adapted to fluidly connect to a dual lumen catheter (not shown) or to two separate catheters, each carrying the fluid injected into one of the wells 402, 404 to an outlet in the bloodstream. Those skilled in the art will understand that forming the F-shaped flow element 410 integrally with the housing 412 of the port device 400 may achieve an additional reduction in the profile dimensions of the port device 400. However, the more complex shape of the housing 412 may increase the cost and/or difficulty of manufacturing the port device 400.

As indicated above, various configurations of the dual well port device comprising an F-shaped flow element used to connect two wells of the port to the lumens of a catheter or to two separate catheters may be employed. In one aspect, the the angular orientation and/or the length of the arms of the F-shaped flow element may be varied to achieve a desired port device profile. In addition, further variations may be made to achieve a desired flow rate through the port device, for example by varying the width and/or cross-sectional shape of the various lumens of the port device and/or F-shaped flow element. The size of the dual well port device and of the F-shaped flow element may also be adjusted by varying the parameters described above, so that the port device may be placed subcutaneously with minimal discomfort to the patient.

The present invention has been described with reference to specific embodiments, and more specifically to a two well port for use with a central venous catheter. However, other embodiments may be devised that are applicable to different medical devices and procedures without departing from the scope of the invention. Accordingly, various modifications and changes may be made to the embodiments, without departing from the broadest spirit and scope of the present invention as set forth in the claims that follow. The specification and drawings are accordingly to be regarded in an illustrative rather than restrictive sense.

What is claimed is:

1. A kit, comprising:
   (a) a port for subcutaneous implantation, the port comprising:
      a housing including at least two wells formed therein; and
      a plurality of outlets, each outlet being in fluid communication with at least one of said wells;
   (b) a plurality of F-shaped flow connectors, each connector comprising:
      a stem connectable to a catheter, the stem having a single outer wall and an inner wall defining first and second lumens therethrough; and
      first and second arms, each arm including a single outer wall defining a single lumen contiguous with one of the first and second lumens of the stem, respectively, and each arm being connectable to one of said outlets; and
   (c) a catheter having a proximal end connectable to a stem of one of said plurality of F-shaped flow connectors and a distal end insertable into a blood vessel of a patient,
      wherein the plurality of F-shaped flow connectors are non-identical, and
      wherein each of the F-shaped flow connectors are characterized by different arm lengths or different stem lengths or different angles formed between the stem and the arms relative to the other F-shaped flow connectors.

2. The kit of claim 1, wherein the first and second wells are positioned along an axis of the housing and wherein the outlets extend from the housing at a first angle relative to the axis, and wherein the arms of one or more F-shaped connectors extend from the stem at an angle approximately equal to the first angle.

3. The kit of claim 1, wherein the port includes at least one flow control valve located between a well and an outlet.

4. The kit of claim 1, wherein each of the F-shaped flow connectors are characterized by different arm lengths relative to the other F-shaped flow connectors.

5. The kit of claim 1, wherein each of the F-shaped flow connectors are characterized by different stem lengths relative to the other F-shaped flow connectors.

6. The kit of claim 1, wherein the first and second arms extend from the stem at first and second angles, and each of the F-shaped flow connectors are characterized by different first and second angles relative to the other F-shaped flow connectors.

7. The kit of claim 1, wherein the F-shaped connectors are reversibly connectable to the outlets.

* * * * *